(12) United States Patent
Buchanan

(10) Patent No.: US 8,408,901 B2
(45) Date of Patent: Apr. 2, 2013

(54) VARIABLE LAND, MULTIPLE HEIGHT FLUTE CONTOUR DESIGN FOR ENDODONTIC FILES

(76) Inventor: L. Stephen Buchanan, Santa Barbara, CA (US)

( * ) Notice: Subject to any disclaimer, the term of this patent is extended or adjusted under 35 U.S.C. 154(b) by 1317 days.

(21) Appl. No.: 11/493,460

(22) Filed: Jul. 25, 2006

(65) Prior Publication Data

US 2007/0026360 A1 Feb. 1, 2007

Related U.S. Application Data

(60) Provisional application No. 60/703,766, filed on Jul. 28, 2005.

(51) Int. Cl.
*A61C 5/02* (2006.01)
(52) U.S. Cl. .......................... 433/81; 433/102
(58) Field of Classification Search ............... 433/81, 433/102, 224
See application file for complete search history.

(56) References Cited

U.S. PATENT DOCUMENTS

| | | |
|---|---|---|
| 4,602,900 A | 7/1986 | Arpaio, Jr. et al. |
| 4,836,780 A | 6/1989 | Buchanan |
| 4,934,934 A | 6/1990 | Arpaio, Jr. et al. |
| 5,219,284 A | 6/1993 | Velvart et al. |
| 5,658,145 A * | 8/1997 | Maillefer et al. ............ 433/102 |
| 5,752,825 A | 5/1998 | Buchanan |
| 5,836,764 A | 11/1998 | Buchanan |
| 5,842,861 A | 12/1998 | Buchanan |
| 5,855,479 A | 1/1999 | Wong et al. |
| 5,871,486 A * | 2/1999 | Huebner et al. ............ 606/305 |
| 5,876,202 A * | 3/1999 | Berlin .......................... 433/102 |
| 5,882,198 A * | 3/1999 | Taylor et al. .................. 433/102 |
| 5,897,316 A | 4/1999 | Buchanan |
| 5,921,775 A | 7/1999 | Buchanan |
| 6,053,735 A | 4/2000 | Buchanan |
| 6,074,209 A * | 6/2000 | Johnson ....................... 433/102 |
| 6,409,506 B1 * | 6/2002 | Graybill ....................... 433/102 |
| 2004/0023186 A1 * | 2/2004 | McSpadden ................ 433/102 |
| 2004/0058298 A1 * | 3/2004 | Brava et al. .................. 433/102 |
| 2005/0026109 A1 | 2/2005 | Buchanan |
| 2005/0214711 A1 | 9/2005 | Buchanan |

* cited by examiner

*Primary Examiner* — Sunil K Singh
(74) *Attorney, Agent, or Firm* — Koppel, Patrick, Heybl & Philpott; Michael J. Ram

(57) ABSTRACT

A tapered endodontic rotary file for shaping or cleaning a root canal in a tooth has one or more flutes spiraling along the length of the file. The diameters of the one or more flutes tapers in a non-uniform manner from a first diameter in a shank portion of the file to a smaller diameter in a tip portion of the file such that at least one flute region intermediate the shank portion and the tip portion has a diameter less than a straight line taper from the shank portion to the tip portion. The flutes can also be landed and the width of the lands can be varied along the length of the file. In particular, the width of the lands in the intermediate region are wider than the width in the tip or shank portion.

9 Claims, 4 Drawing Sheets

VARIABLE LAND, MULTIPLE HEIGHT FLUTE CONTOUR DESIGN FOR ENDODONTIC FILES

This application claims benefit of U.S. Provisional application Ser. No. 60/703,766 filed Jul. 28, 2005.

FIELD OF THE INVENTION

Endodontics is a specialty of dentistry that involves the diagnosis and treatment of root canal pathoses in teeth. Endodontic therapy of teeth with dying or dead pulp tissue requires that the treating dentist prepare an opening into the space inside of the tooth, referred to as the pulp chamber, from which the root canal passageways branch, at their orifices, into each of the roots that support the tooth in the patient's jaw, as shown in FIG. 1. After the dentist negotiates small endodontic files through each canal in the tooth to its terminal point, or its foramina, the canal must be prepared, by using larger files, to have tapered shapes with the largest diameter of the canal at the orifice level and their smallest diameter at their foramina. FIG. 2 shows, a 0.02 ml/ml tapered K file in the canal of the tooth. In a typical K-type file set the taper is 0.32 millimeters on every file over the standard 16 mm length of cutting flutes, or 0.02 mm of taper/mm of flute length. This taper is sometimes referred to as a standard ISO (International Standards Organization) taper. Although these file sets have identical tapers, they come in a number of sizes. The size number 25 characterizing the file (shown in the upper right portion of FIG. 2) is the diameter of the file at the tip in hundredths of a millimeter, and the diameter of the file at the large end is thus 0.32 millimeters greater than this tip diameter. A complete set will include files with 06, 08, 10, 15, 20, 25, 30, 35, 40, 45, 50, 55, 60, 70, 80, 90, 100, 110, 120, 130, and 140 tip sizes, with file sizes from 08 to 60 typically used in procedures. Some manufacturers also make certain half-sizes, or off-standard sizes.

Shaping root canals has been accomplished since the early 1900's by using stainless steel hand files, all with substantially the same relatively small (0.2 mm/mm) taper but with different tip diameters, requiring many different file sizes, many procedural steps, and extensive training to achieve a consistent outcome. In the late 1980's, exotic nickel-titanium alloys having shape memory, extreme flexibility, and remarkable strength were used to fabricate shaping files of greater taper such as shown in FIG. 3 and as described in my U.S. Pat. No. 5,921,775, totally changing the manner in which root canal shaping was done. Because of the increased flexibility of nickel-titanium over stainless steel, files of greater taper were capable of bending around the curvatures commonly encountered in root canals and, because of the added strength, files made of this alloy could be used in dental handpieces without breaking as was common with stainless steel files.

This improvement resulted in more consistent, more ideal shaped canals accomplished with fewer instruments, thus requiring fewer procedural steps which consequently took much less time and required the dentist to have significantly less training and experience. However, these rotary cutting instruments presented their own set of problems, primarily because they cut the root canal walls so rapidly. Since most root canals have some amount of curvature along their lengths, the challenge in designing them became centered around their cutting flute geometries as it was critical that they cut adequately in the hard tissue (dentin) that the roots are made of, but not so effective in cutting the dentin that the file significantly changed the original path of the canal being treated, as shown in FIG. 5 by the canal departure 49.

One of the safest flute designs created was the landed flute as described by Arpaio (U.S. Pat. No. 4,934,934) whereby a narrow portion of the original circumference of the tapered nickel titanium blank was left intact after the helical flute spaces were cut to create the blade edges, as shown in FIGS. 6 and 7. The land reduced the blade edge's aggressiveness as it presented a neutral rake angle to the canal walls being cut during shaping and the land, as it rode the canal wall, prevented the file from threading into the canal or transporting (changing) the path of the canal. The land width could be varied from file to file, making the instrument more or less aggressive in its cutting behavior or, as it was described in my '775 patent, the land width could be varied along the length of the file from the larger shank end to the file tip.

When the land width is increased, it becomes safer in terms of preventing transportation of the canal path during shaping procedures but cuts much slower, increasing the likelihood of breakage due to the cyclic fatigue that builds up with every revolution of the file around a canal curvature. When the land is narrowed, the likelihood of breakage is reduced since fewer revolutions are necessary to accomplish the shaping objective but the chance of changes to the path of a curved canal are increased. When prototypes were made with land widths that were narrow at the larger shank end of the files and relatively wider as the tip end was approached, as described in my '775 patent, the files did not cut significantly faster than those with a consistent, optimized land width along their length but mid-root transportation increased to unacceptable levels.

Another problem encountered during rotary file use that decreases cutting efficiency is that the file can bind along its entire length, creating what is called "taper lock". Taper lock is similar to what occurs when a whittling knife blade is engaged along too much of its length. Resistance to cutting through the piece of wood to be carved is experienced. When taper lock occurs it is tempting for the clinician to add downward pressure on the file to get it to cut further into the canal. However, this is a major cause of instrument breakage. Currently the only way to cut further into a root canal after a file of a certain size stalls out from taper lock is to remove it, switch to a file of narrower or greater taper, and re-introduce the new instrument into the canal where it will engage the dentin along less than its entire length and, as a result, advance further than the previous instrument.

The invention described herein results in a dramatic improvement in the dynamic balance of cutting efficiency and maintenance of the original canal path, particularly when these files are used in curved canals.

SUMMARY OF THE INVENTION

The invention comprises an improved rotary file flute geometry which significantly decreases taper lock, increases cutting efficiency, and also helps to maintain the original path of the canal. This is accomplished by creating multiple heights of contour and multiple land width variations along the length of the file. In a preferred embodiment, the new instrument design has a slightly under-contoured portion, i.e., a narrower waist, in its middle, has thinner lands at the tip and shank regions, and a wider land in the under-contoured mid-region.

BRIEF DESCRIPTION OF THE DRAWINGS

FIG. 5 is a cross sectional view of a tooth during a procedure illustrating unacceptable cutting of the canal wall.

DETAILED DISCUSSION OF THE DRAWINGS

Figure 1:
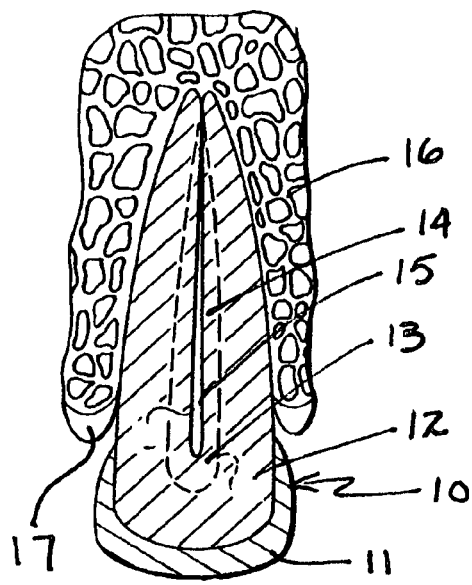
FIG. 1 is a cross sectional view of a tooth in an individuals jaw.

FIG. 1 shows a human tooth 10 composed of enamel 11, dentin 12, the pulp chamber 13, and the root canal space 14 harboring the dental pulp 15 inside. The tooth is embedded in alveolar bone 16, which is covered by gingival tissue 17.

Figure 2:
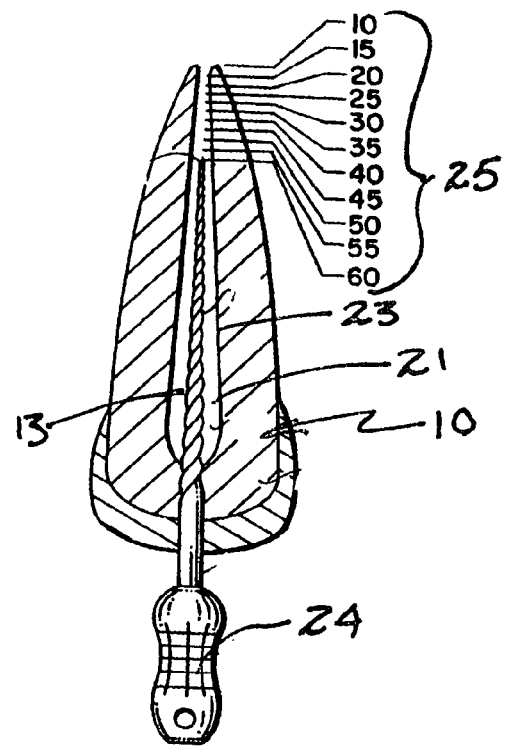
FIG. 2 is a cross sectional view of the tooth of FIG. 1 illustrating a prior art endodontic procedure.

FIG. 2 shows the tooth 10 after an access cavity 21 has been prepared into the pulp chamber 13 and after the root canal 23 has been shaped in a tapered form using a prior art file 24.

Figure 3:
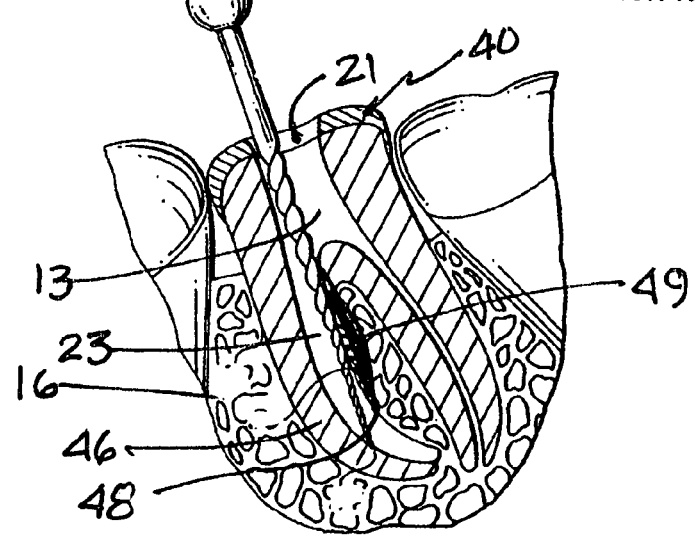
FIG. 3 shows an example of a prior art nickel-titanium file.

FIG. 3 shows a different prior art shaping file 30 with a tip 31, a shank 32, and a handle 33, the file having cutting flutes 34 and a taper portion 35 with a taper 38 of 0.08 mm/mm.

Figures 3, 4, 6, 7:
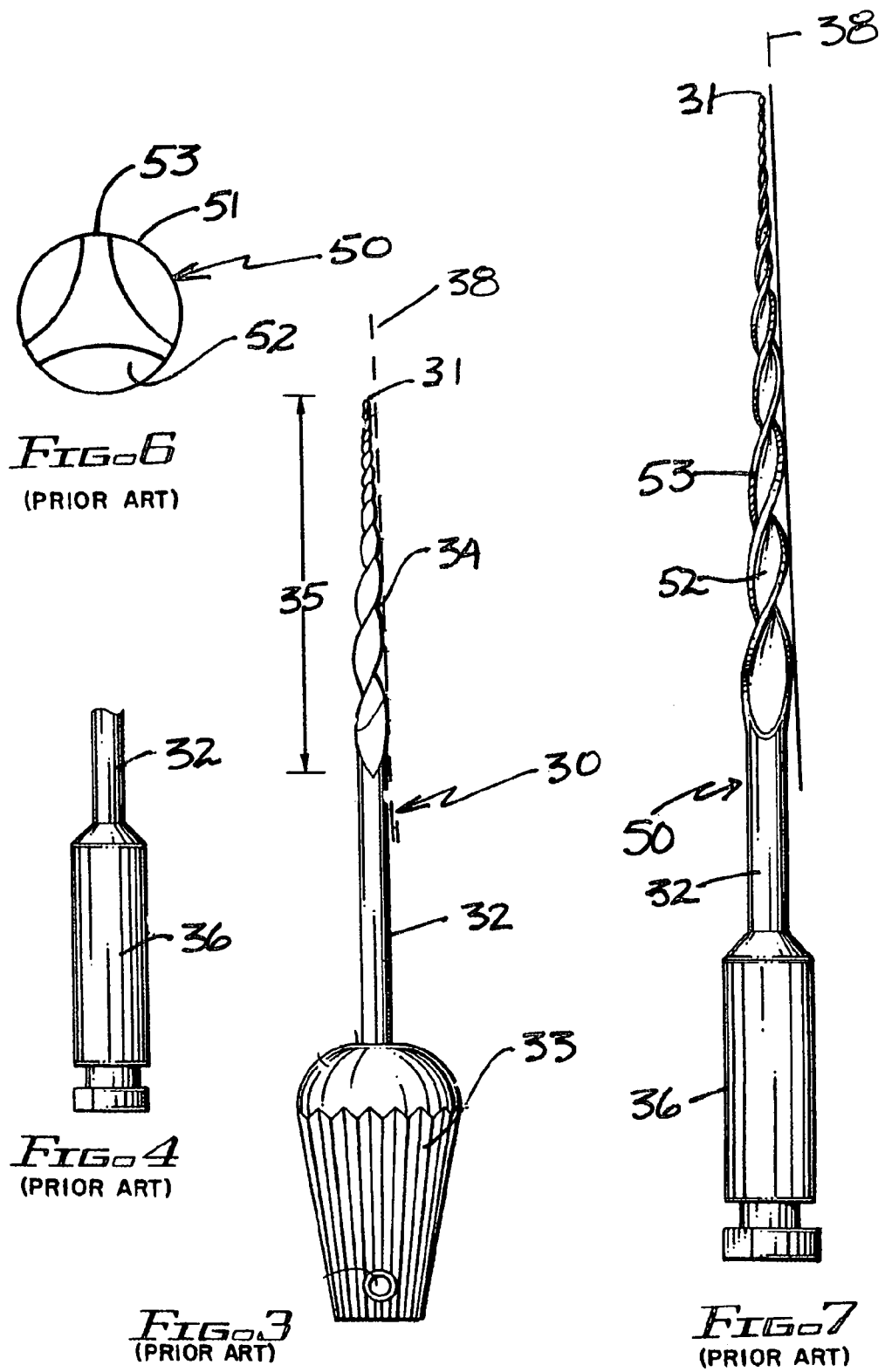
FIG. 4 shows a prior art latch group attachment for a file.
FIG. 6 shows the cross sectional shape of a prior art device.
FIG. 7 is a side view of the prior art device of FIG. 6.

FIG. 4 shows a latch group attachment 36 with shank 32 as an alternative to the handle 33 of FIG. 3

FIG. 5 shows a molar tooth 40 in alveolar bone 16 with an access cavity 21 into the pulp chamber 13 off of which branch the root canals 23. In the mesial root 46 the curved canal 23 has been shaped by a tapered file 24 without landed flutes, causing the mesial root canal 23 path to be straightened to the point of perforating the root wall 48. Infected alveolar bone 49 is seen next to the root perforation. This is a common result of this mishap.

FIG. 6 shows a cross-section of a prior art landed flute file 50 with the original circumference of the wire blank 51, the flute space cutout 52, and the remaining land 53.

FIG. 7 is a side view of the file 50 of FIG. 6 including a tip 31, a shank 32, a latch grip attachment 36, flute spaces 52, and even-width landed flutes 53.

Applicant has now discovered that an improved rotary file can be produced by changing the flute geometry, resulting in a significantly decrease in taper lock, an increased cutting efficiency, and an improved ability to minimize or eliminate cutting into the root wall while maintaining the original path of the canal. Prior art devices have a uniform taper along the lengthy of the file. An improvement disclosed in applicant's earlier patent was to vary the land width. To provide the further improvement in function of the file set forth herein a rotary file has been created that has multiple heights or contours along the length of the taper as well as multiple land width variations along the length of the file. In a preferred embodiment, the new instrument design has a slightly under-contoured portion in the middle of the length of the file, i.e., a narrower waist, and thinner lands at the tip and shank region of the file with wider lands in the narrower contoured, waist mid-region.

The file's slightly narrower "waist" reduces taper lock as a result of the higher contour on the tip and shank regions of the file. Use of instruments with this arrangement provides the practitioner with the ability to use a single instrument to cut all of the required shapes in a root canal procedure instead of the previously required three to four instruments, each with different tapers.

This variable-width land geometry provides more optimal cutting efficiency as a result of the sharper blade portions at the tip and shank regions while the wider land in the mid-region of the file prevents or minimizes straightening of curved canals at their mid-points. Use of these files has shown that sharpening the blades at the tip of the file, where root canals can be quite curved, is safe because of the inherently greater flexibility of that narrower file portion, and that sharpening the blades at the stiffer shank end of the file is safe because the coronal aspects of roots are thicker and straighter than the more apical regions of the root canal.

Figure 8:
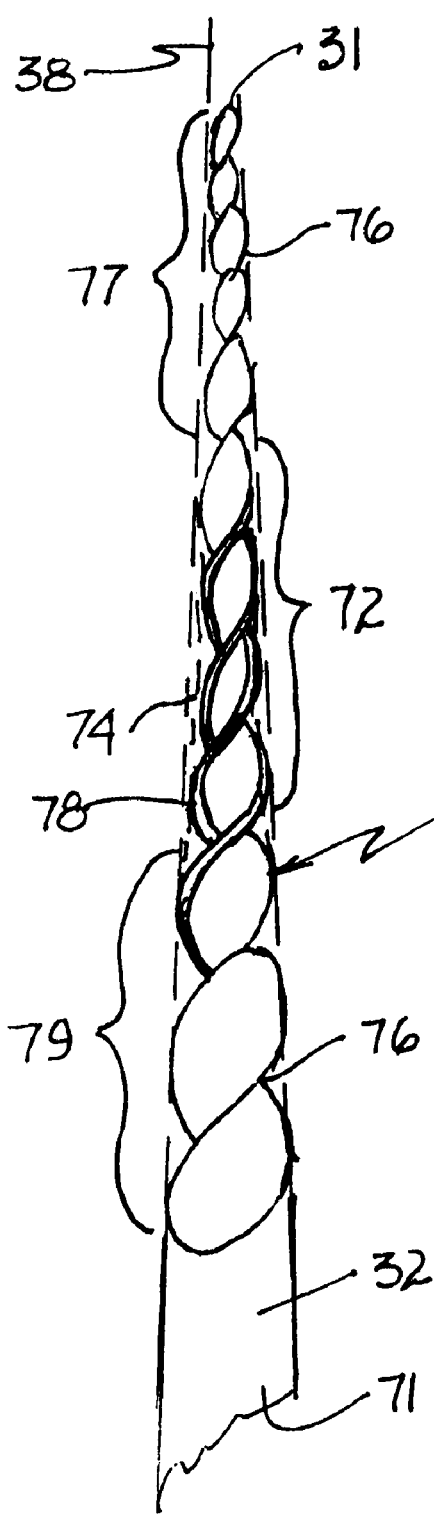
FIG. 8 shows a side view of a file incorporating features of the invention.

FIG. 8 shows a first embodiment of a landed flute file 70 having a tip 31 at the end of a tip region 77 and a shank 32 and adjacent shank portion 79 toward the handle end 71 of the file 70. A mid-region 72 is located between the tip portion 77 and the shank portion 79. A narrower waist contour 74 is located in the mid-region 72. The tip region 77 and the shank region 79 have thin landed flutes 76 while the mid region 72 has wider landed flutes 78.

Figure 9:
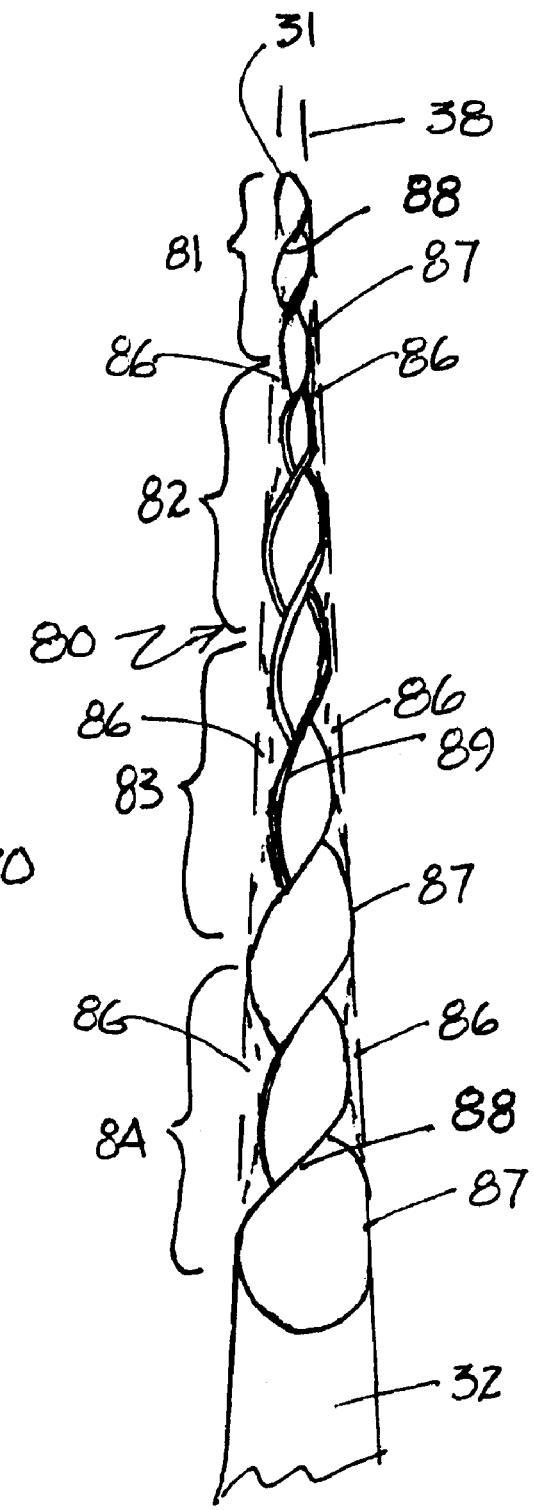
FIG. 9 shows a side view of a second embodiment of a file incorporating features of the invention.

FIG. 9 is a second embodiment of a landed-flute file 80 having a tip region 81, an intermediate region 82 encompassing a length of the file approximately one-quarter to one-half of the distance from the tip 31 along the fluted length of the file 80, a mid-region 83 encompassing a length of the file approximately one-half to three-quarters of the distance from the tip 31 along the fluted length of the file 80 and a shank region 84 adjacent the shank 32 of the file 80. This embodiment includes reduced contours 86 (a reduction of the diameter of the file from the straight taper 38) in the intermediate region 82, mid-region 83 and shank region 84 and increased contours 87 (an increase in the diameter of the file from the decreased region) at the tip, mid-way between the intermediate and mid portions, and at the shank end of the file. This embodiment also has thin flute lands 88 at the shank and tip regions, and wider lands 89 in the intermediate and mid-regions.

Figure 10:
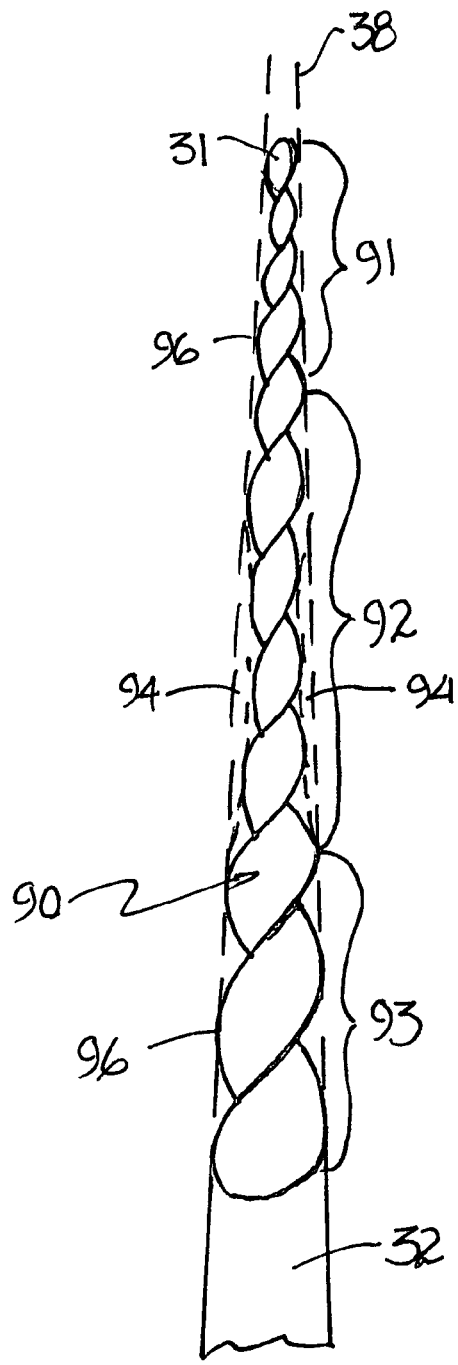
FIG. 10 shows a side view of a third embodiment of a file incorporating features of the invention.

FIG. 10 shows a third embodiment incorporating features of the invention comprising a file 90, without lands, having a tip region 91, a mid-region 92 and a shank region 93. Similar to the second embodiment, this embodiment has a decreased contour 94 in the mid-region 92 and an increased contour 96 in the tip and shank regions 91, 93.

Figure 11:
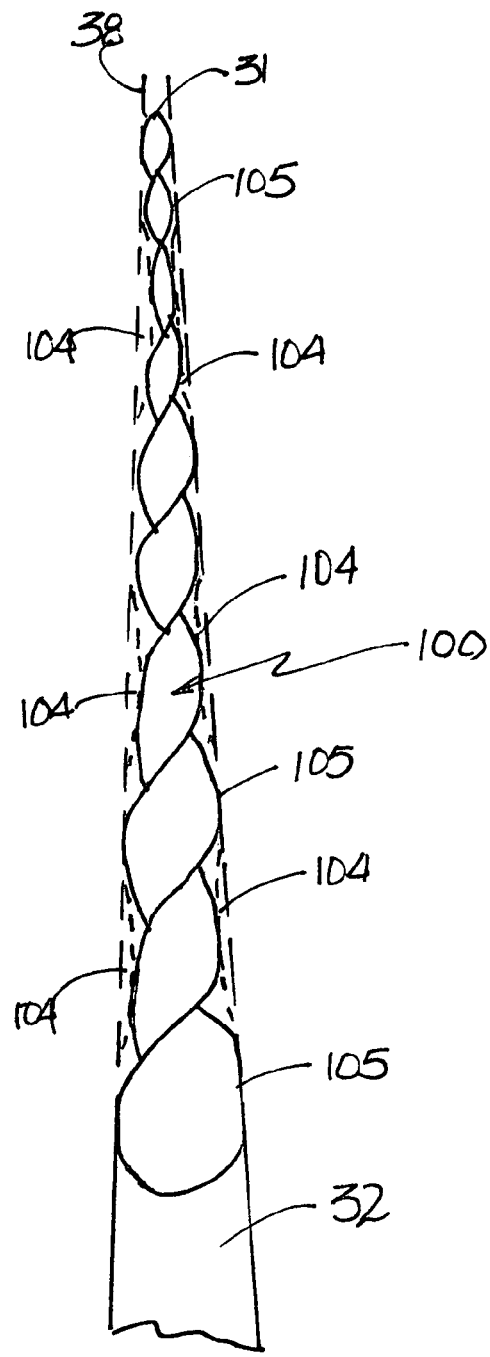
FIG. 11 shows a side view of a fourth embodiment of a file incorporating features of the invention.

FIG. 11 shows a still further embodiment incorporating features of the invention comprising file 100 without lands. Similar to the embodiment of FIG. 9 this embodiment has three portions 104 with a decreased contour and portions therebetween with an increased contour 105 when compared to the adjacent portions.

While the invention is shown and described with four embodiments, it is not intended that the invention be limited to the embodiments shown which have one or three areas with lower contours and the ends and intermediate regions (areas between the lower contour portions) with higher contours. The files can be formed with two reduced contours or four or more lower (decreased diameter) regions dispersed along the length of the file. A basic feature of the invention is that if a straight edge is placed along the length of the file there will be lower portions where the lands do not contact the straight edge. Two sets of files are shown, the first set having wide lands in the decreased contour area and thinner lands in the raised contour area and the second having no lands. However, it is also contemplated that the file can also be made with no lands in one or more portions and lands in other portions. A typical file incorporating features of the invention will have decreased contours with a reduction in diameter from the straight line along the taper of the file from about 0.0001 inches to about 0.004 inches and this region of decreased contour will have a width (distance along the length of the file) of one flute to about one half of the fluted length of the file. Also the width of the lands on the flutes can typically be varied from 0 (no land) to about 0.004 inches. However, a greater depth and length of the decreased contour area or, if there are multiple decreased contour areas, the sum of the lengths of these areas is not outside the scope of the invention. A greater land width can also be used; however, as the land width is further increased the cutting ability of the file generally decreases.

I claim:

1. An improved endodontic instrument for shaping or cleaning a root canal in a tooth comprising a file with one or more flutes spiraling along the length of the file, the one or more flutes having a first outer diameter at a shank end of the file, a second, smaller outer diameter at a tip end of the file, said first and second outer diameters conforming to a straight taper line between a shank portion and a tip portion of the file, the outer diameter of the flutes along an intermediate portion located between the shank portion and the tip portion of the file being less than the first diameter, and a cutting edge on a leading edge of the one or more flutes, wherein the flutes in the shank portion and the tip portion are landed flutes, non-landed flutes or a combination thereof, the improvement comprising:
at least one region in the intermediate portion with flute diameters which are less than the straight taper line between the shank portion and the tip portion wherein the flutes in the at least one region in the intermediate portion are landed flutes and all the lands on the flutes in said one region in the intermediate portion have widths greater than the widths of the lands in the shank portion or tip portion.

2. The improved endodontic instrument of claim 1 wherein two or more regions in the intermediate portion have flute diameters which are less than the straight taper line between the shank portion and the tip portion, said two or more regions being separated by intermediate flutes with larger diameters.

3. The improved endodontic instrument of claim 2 wherein the intermediate flutes with larger diameters conform to the straight taper line.

4. The improved endodontic instrument of claim 1 wherein at least some of the flutes in the shank portion and the tip portion or at least some of the flutes in the shank portion or the tip portion have a land width approximating a cutting edge.

5. A tapered endodontic file for shaping or cleaning a root canal in a tooth comprising one or more flutes spiraling along the length of the file, the diameters of the one or more flutes tapering in a non-uniform manner from a first diameter in a shank portion of the file to a smaller diameter in a tip portion of the file such that at least one flute region between the shank portion and the tip portion has reduced diameter which is less than a straight line taper from the shank portion to the tip portion wherein the flutes in the shank portion and the tip portion are landed flutes, non-landed or a combination thereof, the flutes at least in the intermediate flute region are landed flutes and all of the lands on the flutes in the intermediate flute region have widths greater than the widths of the lands in the shank portion or tip portion.

6. The endodontic file of claim 5 wherein two or more regions in the intermediate portion have flute diameters which are less than the straight line taper between the shank portion and the tip portion, said two or more regions being separated by intermediate flutes with larger diameter.

7. The endodontic file of claim 6 wherein the intermediate flutes with larger diameters conform to the straight line taper.

8. The endodontic file of claim 5 wherein the tip portion of the file comprises 25 to 50 percent of the fluted length of the file and the fluted region intermediate the tip portion and the shank portion comprises an adjacent portion, the tip and region intermediate in combination comprising 50 to 75 percent of the fluted length of the file.

9. The tapered endodontic file of claim 5 wherein at least some of the flutes in the shank portion and the tip portion or at least some of the flutes in the shank portion or the tip portion have a land width approximating a cutting edge.

* * * * *